United States Patent [19]

Shakkottai et al.

[11] Patent Number: 4,876,889
[45] Date of Patent: Oct. 31, 1989

[54] ACOUSTIC HUMIDITY SENSOR

[76] Inventors: Parthasarathy Shakkottai, 2622 Gardi St., Duarte, Calif. 91010; Eug Y. Kwack, 20946 E. Canyon Ridge Rd., Walnut, Calif. 91789; Shakkottai P. Venkate-Shan, 34, III Main Rd., Gandhi Nagar, Adyar Madras, India, 600020

[21] Appl. No.: 215,374

[22] Filed: Jul. 5, 1988

[51] Int. Cl.$^4$ .................. G01W 1/02; G01N 29/02
[52] U.S. Cl. .................. 73/336.5; 73/597; 374/119
[58] Field of Search .................. 73/335, 336.5, 24, 29, 73/597; 374/119; 236/44 C

[56] References Cited

U.S. PATENT DOCUMENTS

| | | | |
|---|---|---|---|
| 4,083,765 | 4/1978 | Lawson | 204/195 W |
| 4,255,964 | 3/1981 | Morison | 73/24 |

FOREIGN PATENT DOCUMENTS

| | | | |
|---|---|---|---|
| 205186 | 12/1986 | European Pat. Off. | 73/335 |
| 205536 | 12/1983 | German Democratic Rep. | 73/336.5 |
| 1016752 | 5/1983 | U.S.S.R. | 73/336.5 |

OTHER PUBLICATIONS

Lawson et al., Humidity Measurements by Polymer Electrolytic Hygrometer for Harsh Environments, Sensor Expo 1987, pp. 49–59.
Rotronic Instruments Corp., Humidity-Temperature Transmitter.
Pacer Systems, Inc., "Vaporsense 1000".
Honeywell Brochure, Capacitive Solid State Dew Point Hygrometer.
Vaisala Inc., Econ 200—The New Industrial Dew Point Measuring System.
Venkateshan et al., "Acoustic Temp Profile Measurement Technique for Large Combustion Chambers", ASME Paper 87-WA/HT-14, Submitted as Disclosure 07/108813 on 10/15/87, Found Allowable on 05/16/88.

*Primary Examiner*—John Chapman
*Assistant Examiner*—Joseph W. Roskos

[57] ABSTRACT

The water vapor content for air in drier ducts, ovens, furnaces and the like is determined by a measurement of sound speed which is done by measuring the time difference between sound pulses reflected by two reflectors spaced a known distance apart in a guide tube. The transmitter-receiver is located at one end of the tube. The tube has enough number of holes to allow the hot moist air to get into the probe tube. A non-porous tube containing dry air placed in the same duct provides a similar measurement of dry-sound speed. The ratio of the two speeds of sound or the two measured time intervals is a simple function of the water vapor content practically independent of temperature thereby providing a very accurate measurement of water vapor content over an extremely wide range of temperatures. The sensor is accurate, immune to harsh environments, has an extremely low time constant, has absolutely no hysteresis and needs no calibration.

10 Claims, 5 Drawing Sheets

ACOUSTIC HUMIDITY SENSOR

BACKGROUND OF THE INVENTION

1. Field of the Invention

The present invention is directed to a system for measuring the water vapor content in drier ducts, ovens and the like. By measuring the sound speed in the medium and also in a reference tube containing dry air at the same temperature, a sensor which measures the water vapor independently of temperature is made possible. In addition, no calibrations are required, all the data being obtained by measurements of two time intervals which can be done to high accuracy. The sensor has virtually no temperature limit for all industrial applications.

2. Description of the Prior Art

Moisture measurements are necessary for the control of industrial processes where drying is involved. For example control of drying of paper in a paper mill requires a trouble-free rugged sensor for humidity control. Many industrial environments are harsh. High temperature, chemical corrosion or contamination are problems that make many types of humidity sensors unreliable in operation.

Polymer hygrometers of a particularly rugged type have been described by D. D. Lawson (U.S. Pat. No. 4,083,765) using a fluorocarbon polymer containing sulphonic acid groups. This polymer is called nafion and is made by DuPont. Its conductivity depends on water vapor content and temperature. A variation of this polymer with lithium doping has been shown to be immune to degradation from dust and organic vapors in a paper mill at temperatures near 65° C. and air stream speeds of 40 ft/sec. (ref. 2). The sensor output is linear over a limited region of humidity and temperature.

Polymers which absorb water have been used as humidity sensors using a measurement of capacitance. This type is made by Rotronic Instrument Corporation (ref. 3).

Pacer systems offers a moisture sensor based on absorption of ultraviolet light by moisture (ref. 4). The probe is claimed to withstand 250° C. Keeping the optical windows clean is difficult.

Dew Point Hygrometers are also used. Thermoelectric cooling of a surface makes dew settle on the surface whose property is detected by a change of light reflection, capacitance change (ref. 5) or attenuation of surface acoustic waves (ref. 6). Such sensors are not immune to the presence of containments such as dust and oil vapors.

OBJECTS AND SUMMARY OF THE INVENTION

It is a primary object of the present invention to provide a system for obtaining the water vapor content of hot air in harsh industrial environments, in moving or quiescent air, particularly at high temperatures where most humidity sensors do not survive.

It is another object to produce a sensor practically independent of temperature over an extremely wide range of temperature, there being virtually no temperature limit for operation of the sensor.

Yet another objective is to produce a sensor which does not need any calibrations at standard conditions of humidity or temperature.

The principle on which the sensor is based is the simple dependence of the speed of sound of a mixture of gases on temperature and on composition. The ratio of the speed of sound in air containing water vapor to the speed of sound in dry air at the same temperature is a function of essentially only the water vapor content. The relationship is linear in water vapor content at small values up to a partial pressure equal to 250 mm Hg. The exact, slightly nonlinear relationship is well known, however.

The sound speed is measured by reflecting a sound pulse from two reflectors contained in a tubular guide separated by a suitable distance over which the average sound speed is sought. In ducts and ovens lengths of the order of 1 m would be suitable. The time difference between the two reflected pulses is inversely proportional to the speed of sound. Two wave guide tubes located near each other are used, one containing dry air for reference and another, which is porous, containing the moist air in the oven. The ratio of time intervals obtained from the two tubes is equal to the ratio of sound speeds in moist and dry air at the same temperature and is a unique function of moisture content virtually independent of temperature. The sensor, being essentially a tube of stainless steel, will withstand temperatures far higher than that of any environment whose moisture content is sought.

The sensor has many valuable advantages for industrial applications. It is immune to dust, fibers, chemicals, and condensation of water if it occurs, as it does occasionally, in drier ducts. There is no need to calibrate the sensor at known humidity environments. This immediately eliminates many uncertainties that exist with hygrometers which change their properties on exposure to harsh environments. There is absolutely no hysteresis as in other hygroscopic humidity sensors. The time constant of the acoustic sensor is extremely short and depends only on the averaging time of the counters. It can be as short as 1 ms if a single-shot signal capturing device is used!

The only disadvantage of this sensor is that it can be somewhat too bulky for some applications.

BRIEF DESCRIPTION OF THE DRAWINGS

A more complete appreciation of the invention and the attendant advantages thereof will be more clearly understood by reference to the following drawings wherein.

DESCRIPTION OF THE PREFERRED EMBODIMENTS

Figure 1:
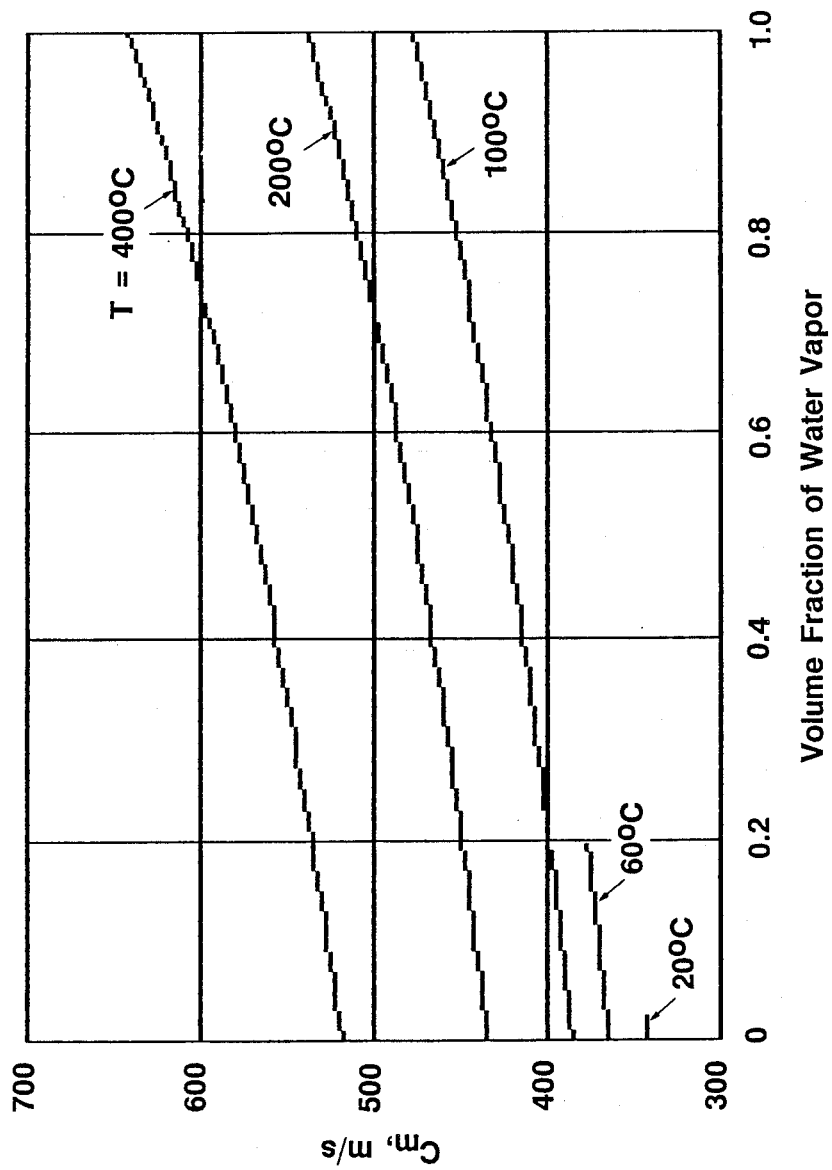
FIG. 1 is a plot of the sound speed of moist air, $C_m$, versus the volume fraction of water vapor at temperatures equal to 20°, 60°, 100°, 200° and 400° C., showing that $C_m$ increases with both water vapor content and temperature in a regular manner.

The system for measurement of sound speed is essentially the system for temperature profile measurement in large furnaces and kilns and method therefor, a disclosure filed by P. Shakkottai and S. P. Venkateshan on 10/15/87 with the Ser. No. 07/108,813, which has been examined and found allowable for insurance of Letters Patent. The present system is somewhat simpler because humidity profiles are seldom required, a single average measurement being usually the only quantity required. The guide tubes are modified to allow the humid air to go into the sensor tube by drilling a number of holes in the tube.

Speed of Sound of Mixtures

The internal energy of a unit mass of a mixture of perfect gases u, heat supplied q and work done by pressure p in a change of specific volume v are related by $$du = dq - p\, dv, \quad (1)$$

which under adiabatic conditions is simply, $$du = -pdv = -pd(1/\rho), \quad (2)$$

where $\rho$ is the density of the mixture. Denoting $c'_{vi}$ to be the specific heat of a single molecule of species i, changes of internal energy with temperature of unit mass of a mixture is also given by $$du = \Sigma c'_{vi} n_i v\, dT = \Sigma c'_{vi} n_i dT/\rho, \quad (3)$$

where $n_i$ is the number of molecules per unit volume. The equation of state for the mixture is $$p = \Sigma n_i kT, \quad (4)$$

where k is the Boltzmann constant. The density of the mixture is given by $$\rho = \Sigma n_i m_i, \quad (5)$$

where $m_i$ is the mass of 1 molecule of gas i. Using these equations, T must be eliminated. From (4) and (5), $$d(p/\rho) = p\, d(1/\rho) + dp/\rho = \Sigma n_i k\, dT/\Sigma n_i m_i. \quad (6)$$

From (2) and (3), $$dT = \rho du/\Sigma c'_{vi} n_i = -\rho p d(1/\rho)/\Sigma c'_{vi} n_i \quad (7)$$

From (6) and (7), $$pd(1/\rho) + dp/\rho = \frac{\Sigma n_i k}{\Sigma n_i m_i} \frac{(-\rho p)d(1/\rho)}{\Sigma c'_{vi} n_i} \quad (8)$$

$$= \frac{\Sigma n_i k}{\Sigma c'_{vi} n_i} (-p)d(1/\rho)$$

From (5), (6) and (7), dT may be eliminated to get for the square of the speed of sound C the equation $$C = dp/d\rho = (1 + \Sigma n_i k/\Sigma n_i c'_{vi}) p/\rho \quad (9)$$

The specific heat for a single molecule is simply equal to kf/2 because each degree of freedom is associated with an energy equal to kT/2 and there are f degrees of freedom. Using this, $$C^2 = (1 + 2\Sigma n_i/\Sigma n_i f_i)(\Sigma n_i kT/\Sigma n_i m_i) \quad (10)$$

This relation depends on T, masses of molecules $m_i$, number densities $n_i$ and degrees of freedom $f_i$, which are all known.

For dry air the fraction number densities, molecular weights, and degrees of freedom are tabulated below.

| i | gas | $n_i/\Sigma n_i$ | $m_i/m_H$ | f |
|---|-----|------------------|-----------|---|
| 1 | $N_2$ | 0.779 | 28 | 5 |
| 2 | $O_2$ | 0.209 | 32 | 5 |
| 3 | Ar | 0.009 | 40 | 3 |
| 4 | $CO_2$ | 0.003 | 44 | 6 |
| 5 | $H_2O$ | 0.000 | 18 | 6 |

Using these, $C^2$ can be calculated for dry air and for air containing a volume fraction $n_5/\Sigma n_i$ of water vapor.

In FIG. 1, the speed of sound of moist air, $C_m$, is plotted versus the volume fraction of water vapor at temperatures equal to 20°, 60°, 100°, 200° and 400° C. These curves show that $C_m$ increases with both temperature and volume fraction. The curves are almost straight and parallel.

Figure 2:
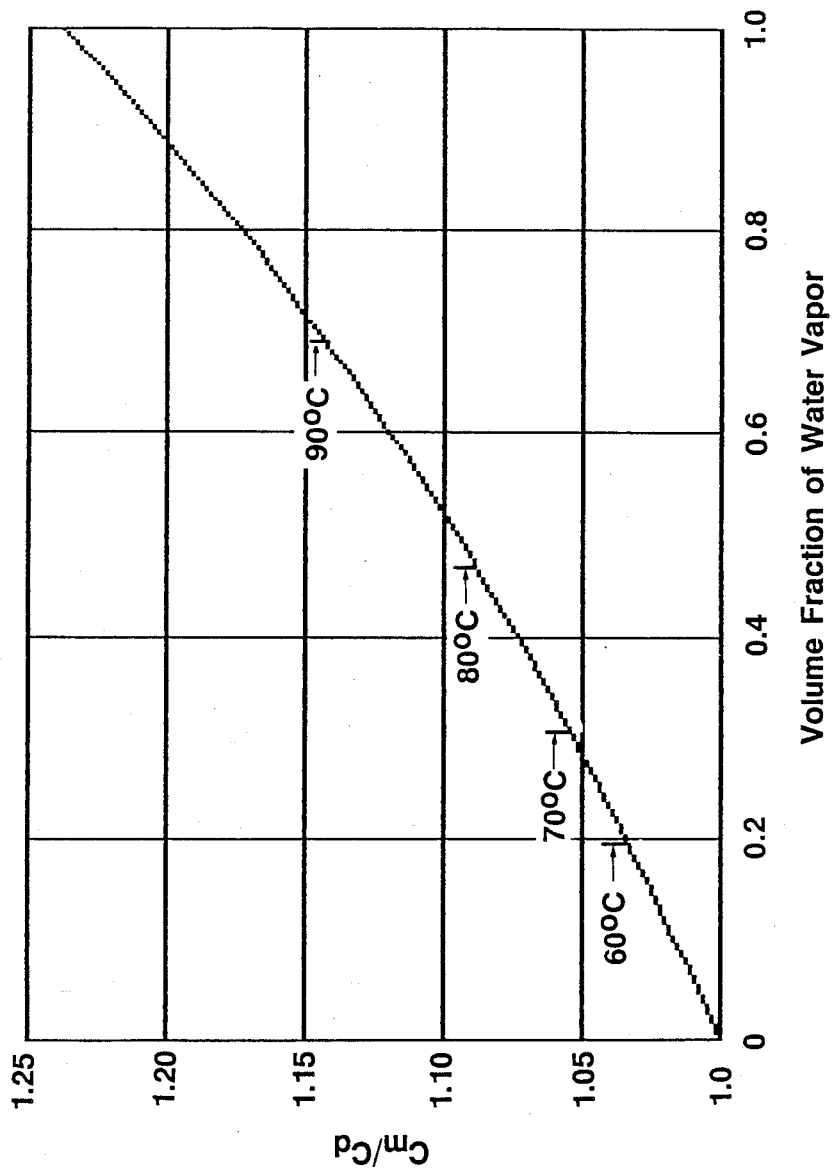
FIG. 2 is a plot of $C_m/C_d$, the ratio of sound speed of moist air to that of dry air vs. volume fraction showing that there is no temperature dependence; the temperatures indicated along the curve representing the maximum values of water vapor content at that temperature.

FIG. 2 shows the ratio of speed of sound in the moist air $C_m$, to the speed in dry air, $C_d$, as a function of volume fraction of water vapor. This curve is not dependent on temperature. Values of temperatures marked along this curve refer to conditions of saturation or of 100% relative humidity. At and above 100° C., the volume fraction can reach 1.00. In general, the volume fraction will be less than 1.

Estimates of error

In deriving (10), fixed numbers of degrees of freedom were associated with different species. In reality, as temperature increases, more degrees of freedom are excited. To estimate errors from this variation, the speed ratio is calculated from gas tables where the specific heats of dry air and of water vapor are available directly. These calculations are performed by determining the gas constant R and the mass weighted averages of specific heats of the mixtures to find the ratio of specific heats, $\gamma$, and hence $$C = (\gamma RT)^{1/2} \quad (11)$$

Figure 3:
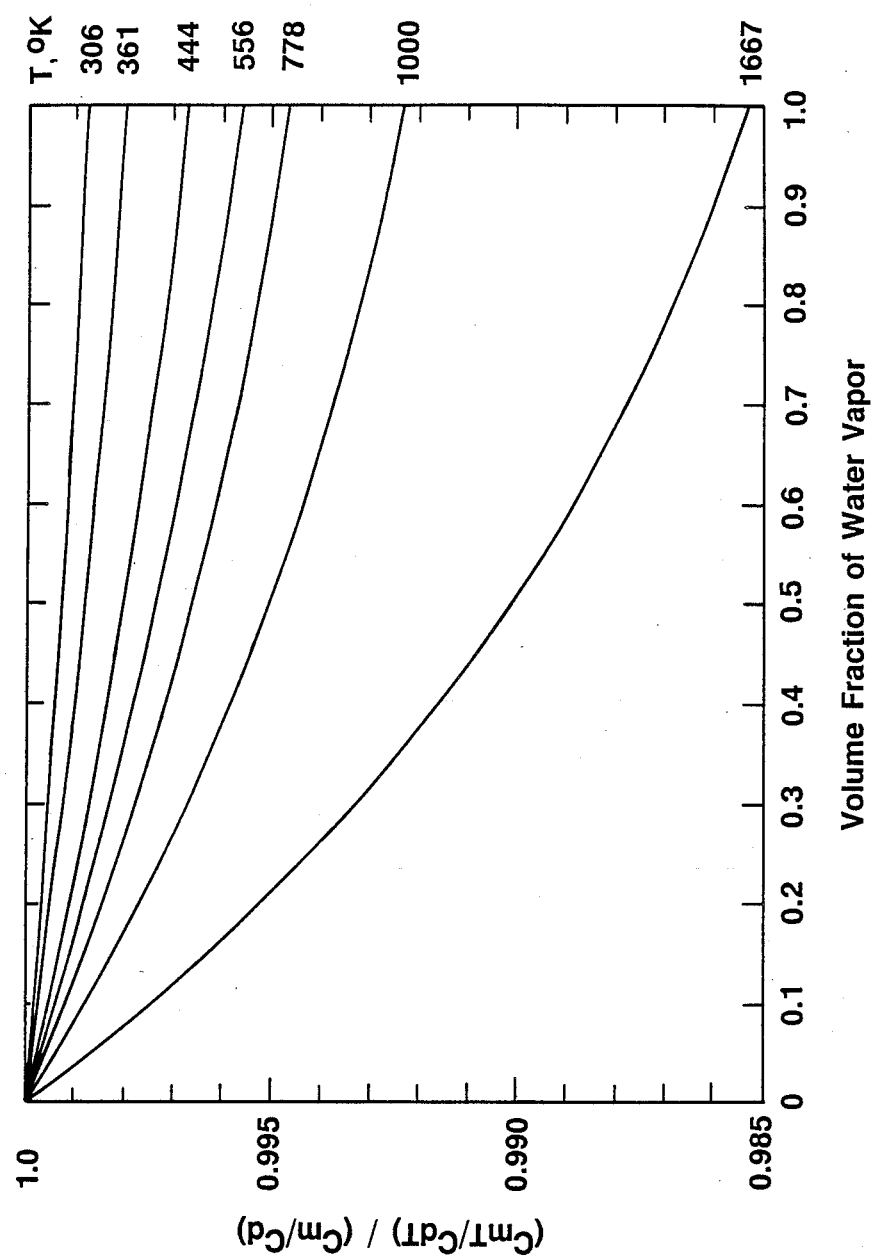
FIG. 3 is a plot of $(C_{mt}/C_{dt}) \div (C_m/C_d)$ vs. water vapor content where the subscript t refers to quantities obtained from standard gas tables; the above ratio represents the error in using fixed degrees of freedom for the calculation of $(C_m/C_d)$, the error being quite small as shown by the greatly enlarged vertical scale.

The ratio $C_{mT}/C_{dT}$ represents the speed ratio obtained from gas tables. The quantity $(C_{mT}/C_{dT}) \div (C_m/C_d)$ should ideally be unity. Departures from this value are due to effects of varying degrees of freedom of molecules. The above quantity is plotted in FIG. 3 versus the volume fraction of water vapor at various temperatures equal to 306°, 361°, 444°, 556°, 778°, 1000° and 1667° K. at which tabulated data were available. The ratio on the y axis has a very enlarged scale. Most of the characteristic lines are within 1% showing that the approximation involved in using fixed degrees of freedom is quite good. The curve for $C_m/C_d$ given in FIG. 2 as a function of the volume fraction x can be represented by $$C_m/C_d = 1 + 0.148x + 0.0884x^2 \quad (12)$$

The maximum difference in $C_m/C_d$ between the Eq. (12) and the curve in FIG. 2 is only 0.13%. Determination of x is therefore simplified by use of Eq. (12) to $$x = (11.312 \, C_m/C_d - 10.611)^{\frac{1}{2}} - 0.837. \quad (13)$$

valid within 1% error from 330° to 1000° K.!

The humidity sensor

Figure 4:
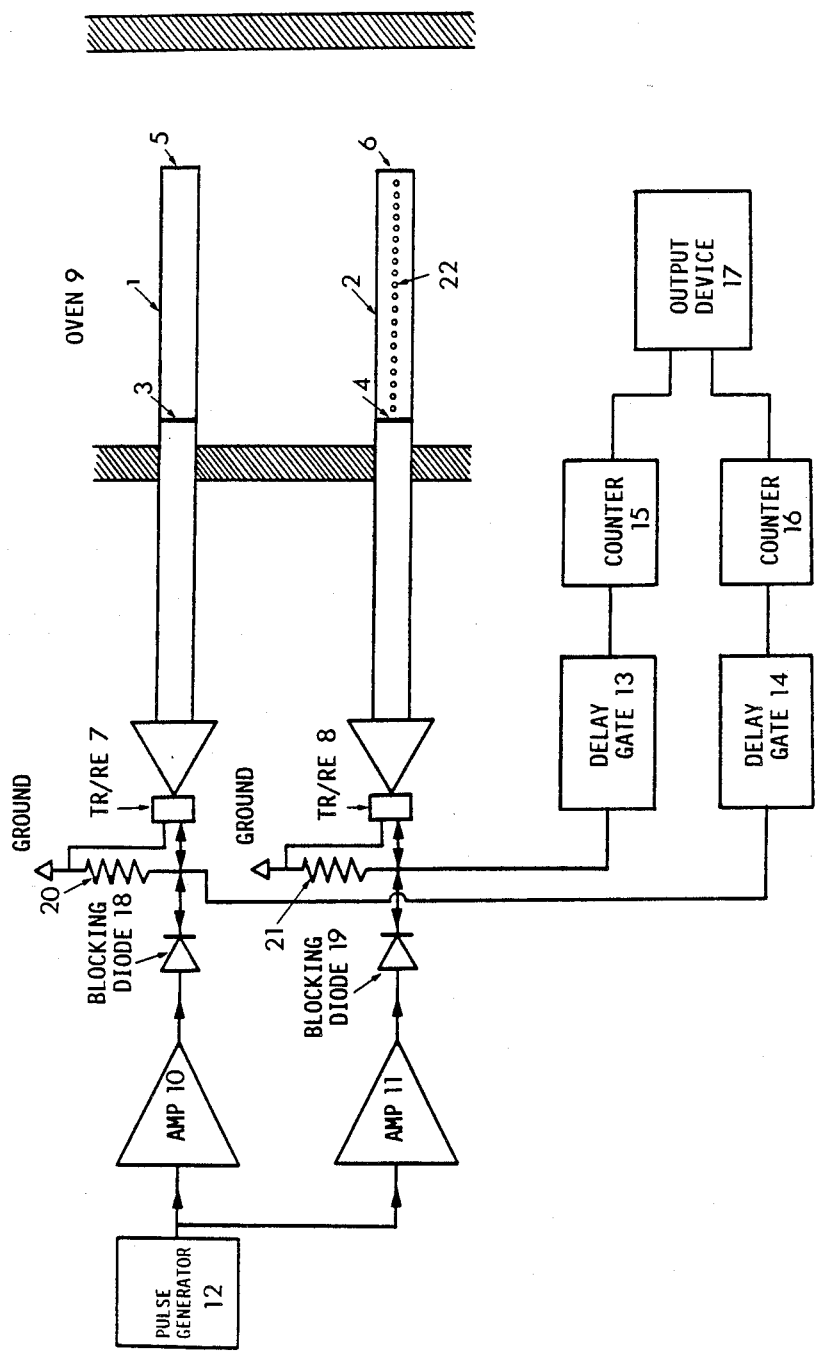
FIG. 4 is a sketch showing the dual sensor tubes in an oven, one containing dry air and the other being porous to allow the moist air to enter the region between the reflecting stub and end wall, driven by two transmitters located outside the oven at the end of the sensor tubes by a common pulse generator, the transmitters also acting as receivers and dual signal processing chains containing delay gates, counters and an output device (microcomputer) to display measured temperature and water vapor content.

A sketch of the humidity sensor is shown in FIG. 4 where two sensor tubes, one porous 2 and the other non-porous are shown. The moist environment in the oven 9 is sensed by tube 2 whereas tube I is filled with dry air. Sound pulses reflected from the stub 3 (a diametral rod) and the end wall 5 have a time interval which is equal to twice the separation between the stub 3 and end wall 5 divided by the speed of sound $C_d$ in dry air. Similarly, the time interval between the reflected pulses from stub 4 and end wall 6 is determined by the speed of sound $C_m$ of the moist air in tube 2. The pulses are generated by transmitter-receivers 7 and 8 driven by amplifiers 10 and 11 by a common pulse generator 12. The time intervals are measured by two counters 15 and 16 discarding the initial transmitted pulse by using delay gates 13 and 14. The ratio of the two time intervals is converted to the water vapor content and is displayed by 17. Also, temperature measured by the sensor tube I is also displayed by the output device 17. Print outs, alarms and control signals could also be produced by using a microprocessor in 17.

A blocking diode 18 prevents short circuiting of return pulses by the output amplifier 10 and also prevent oscillations in the reverberant environment inside the sound guides. The termination resistor 20 is also shown. Similarly, diode 19 and resistor 21 are used for the other tube 2.

The sensor tube 2 is made porous by drilling holes 22 of such size and number that adequate ventilation is obtained without excessive sound reflections. The holes also reflect sound waves. One acceptable design arrived at experimentally using a 1 inch sensor tube consists of 100 holes of diameter 3/32 inch spaced 1 inch apart, four to a circumference, along a tube occupying a length equal to 25 inches. Even larger holes up to $\frac{1}{8}$ in diameter can be used successfully because more baseline noise can be tolerated. The noise is not the usual random noise but represents the fixed coherent rumble caused by the holes which repeats from pulse to pulse. The porosity of this configuration is approximately 1%.

Typical Signals and Measurement Accuracy

Figure 5:
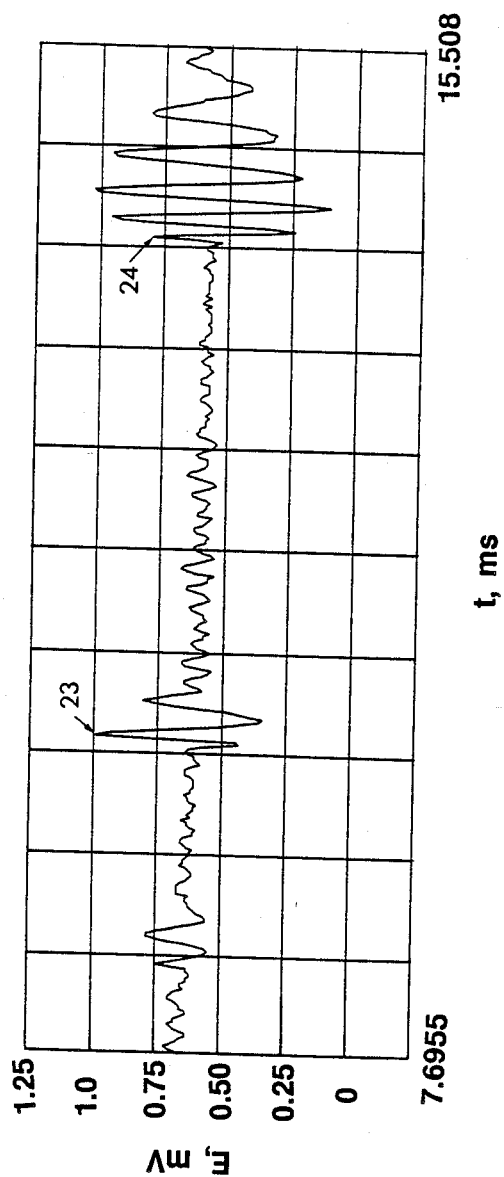
FIG. 5 is a sample record of pulses reflected in dry air from a stub and end wall, with 100 holes of 3/32 inch diameter between the stub and end wall, showing the presence of sharp peaks in the pulses and also the presence of small $c'$. oscillations between the pulses caused by the holes, the digital device enabling the time interval between peak 23 and peak 24 to be measured to 3 decimal places as 3.844 ms.

A typical signal record showing the pulse 23 reflected from the stub 3 and the pulse 24 reflected by the end wall 5 is shown in FIG. 5. The reflection 25 from the holes is seen present between the two pulses as a general rumble. To obtain the round trip transit time of sound waves, the time interval between the first positive peaks in pulses 23 and 24 is measured. This can be done to 3 decimal places using the electronic cursor in the signal analyzer that was used in this particular case. For example, in the record shown it is 3.844 ms. The ratio $C_m/C_d$ ($=t_d/t_m$) can be determined to three decimal places easily. A number like $1.123 \pm 0.001$ represents an error on the order of $\pm 0.004$ in vapor volume fraction because the full scale value of $C_m/C_d$ in FIG. 2 is only 1.250 which differs from 1 by 0.250. This shows that determinations of volume fraction to 0.5% is easily done independent of temperature in the region of 50% water vapor fraction. At lower humidity values, the same error will be larger if only 3 decimal place accuracy is achieved in the above ratio. However, it is possible to get one more decimal place in timing, by averaging over many pulses. In summary, it is possible to get an accuracy of 0.5% over a wide range of water vapor content.

REFERENCES

1. D. D. Lawson, U.S. Pat. No. 4,083,765, "Polymer Electrolytic Hygrometer," Apr. 11, 1978.
2. D. D. Lawson, P. Shakkottai, S. P. Venkateshan. "Humidity Measurements by Polymer Electrolytic Hygrometer for Harsh Environments," Proceedings of Sensors Expo, Detroit, Mich., Sept. 15, 1987, pp. 49–59.
3. Rotromic Instrument Corporation brochure, Humidity-Temperature transmitter HT-150 Series.
4. Pacer Systems Inc , "Vapor Sense 1000," brochure.
5. Capacitive Solid State Dew Point Hygrometer, Honeywell brochure.
6. Vaisala Inc., Dew Point Sensor DEWCAP in ECON 200—The new Industrial Dewpoint Measuring System.

The embodiments of the invention in which an exclusive property or privilege is claimed as defined as follows:

1. An acoustic time-of-flight method for deriving data indicative of average gas temperature and average water vapor content in humidity chambers, ovens, driers, furnaces and the like comprising the steps of:
    (a) installing a closed tubular sensor containing dry air and allowing it to come to equilibrium with hot, moist air in one of said chambers, ovens, driers, or furnaces,
    (b) transmitting sound pulses from the cold end of said tubular sensor and allowing said pulse to propagate through said dry air,
    (c) receiving sound pulses partially reflected from both a stub or other reflecting means located in said sensor and the end wall,
    (d) measuring a time difference between said reflected pulses,
    (e) synchronously transmitting sound pulses in a second tubular sensor of identical size as the first said tubular sensor, but containing many holes in the region between its end wall and stub or other reflecting means, to allow moist environment of said chamber, oven, drier or furnace to be present inside said second sensor,
    (f) receiving sound pulses as in (c) partially reflected from the end wall and from said stub or other reflecting means located at the same distance from said end wall as in the first sensor,
    (g) measuring a time interval between said pulses in (f), (h) forming a ratio of time intervals found in (d) and (f) which is equal to ratio of speeds of sound in moist air and in dry air, (i) and calculating the volume fraction of moisture which is related only to said speed of sound ratio in (h) independently of said air temperature in said chamber, oven, drier or furnace, over an extremely wide range of temperatures.

2. A system for processing signals and deriving moisture content and temperature of hot, moist air in ovens, driers, furnaces and the like comprising: Two tubular sensors of heat and moisture resistant material containing two sound reflectors in each said sensor tube, one being a diametral stub and the other being the end wall of said sensor tube; adequate porosity in the form of a large number of small holes in the region between said reflectors in one said sensor tube to allow free entry of said moist air from said drier or furnace, the other said sensor tube being airtight and containing dry air for reference; two transmitter receiver means mounted outside said oven or furnace at the cold ends of both said sensor tubes; two power amplifiers to drive said transmitter-receiver means; an isolating diode between said transmitter-receiver means and said power amplifier to suppress unwanted oscillations and to prevent short circuiting of received pulses by said power amplifier; a pulse generating means to drive both said transmitter-receiver means simultaneously in a controlled manner; two signal processing means consisting of pre-amplifiers, time gates and counters to process detected pulses reflected by said reflectors in each said sensor tube; output means for calculating and displaying said temperature and said moisture content from said measured time intervals between said reflected pulses.

3. A system as described in claim 2 wherein said sensor tubes are between 30 cm and several meters in length, depending on the size of said oven, drier or chamber.

4. A system as described in claim 2 wherein the diameter of said sensor tubes ranges from a few mm to 50 mm.

5. A system as described in claim 2 wherein the material of said sensor tubes is resistant to high temperature and humidity, most commonly stainless steel.

6. A system as described in claim 2 wherein the distances between said stub and said end wall are the same for both said sensor tubes and can be chosen between 30 cm to a few meters, as required.

7. A system as described in claim 2 wherein the duration of said pulses is adjusted such that a typical wave length in said sound pulse is greater than the diameter of said sensor tubes such that only plane waves propagate. Typically, a pulse width of 0.1 ms corresponding to a bandwidth of 10 kHz has typical wavelength equal to 3.5 cm at room temperature in dry air and would be suitable for a sensor tube of diameter equal to 1.25 cm.

8. A system as described in claim 2 wherein a single ended transmitter-receiver means mounted at the cold end of said sensor tubes is used to probe said sound speeds of the media within said tubes.

9. A system as described in claim 2 wherein said pulses of sound are repeated at time intervals larger than the round trip travel time from said transmitter-receiver to said end wall.

10. A system as described in claim 2 wherein a signal source drives both said transmitter-receivers simultaneously to increase accuracy of measurements of time difference between said reflected pulses.

* * * * *